United States Patent [19]
Green et al.

[11] Patent Number: 4,818,528
[45] Date of Patent: Apr. 4, 1989

[54] VACCINE AGAINST INFECTIOUS BOVINE KERATOCONJUNCTIVITIS

[75] Inventors: Wallace H. Green, Scottsville, N.Y.; Leon N. D. Potgieter, Knoxville, Tenn.

[73] Assignee: The University of Tennessee Research Corporation, Knoxville, Tenn.

[21] Appl. No.: 11,991

[22] Filed: Feb. 6, 1987

[51] Int. Cl.$^4$ ............................................. A61K 39/02
[52] U.S. Cl. ...................................... 424/92; 424/93; 435/822
[58] Field of Search .................... 424/92, 93; 435/822

[56] References Cited

U.S. PATENT DOCUMENTS

| | | | |
|---|---|---|---|
| 3,197,373 | 7/1965 | Jackson | 424/92 |
| 3,401,219 | 9/1968 | Zeissig | 424/92 |
| 4,254,098 | 3/1981 | Graham et al. | 424/92 X |
| 4,539,201 | 9/1985 | Gwin | 424/92 |
| 4,675,176 | 6/1987 | Gerber | 424/92 |

FOREIGN PATENT DOCUMENTS 0107845  5/1984  European Pat. Off. .
0146523  6/1985  European Pat. Off. .

OTHER PUBLICATIONS

A Pilus Peptide Vaccine for the Prevention of Gonorrhea, G. K. Schoolnik, J. Y. Tai, E. C. Gotschlich, Prog. Allergy, vol. 33, pp. 314–331, (Karger, Basel 1983).
The Human Erythrocyte Binding Domain of Gonoccocal Pili, G. K. Schoolnik, J. Y. Tai, E. C. Gotschlich, Bacterial Vaccines, vol. 4, Thieme Slitton, New York, 1982, 172–180.
Cloning and Sequencing of a Moraxella bovis Pilin Gene, Carl F. Marrs, Gary Schoolnik, J. Michael Koomey, Jonathan Hardy, Jonathan Rothbard and Stanley Falkow, Journal of Experimental Medicine, vol. 163, No. 1 pp. 132–139 Jul. 1985.
Gonococcal Pili, Primary Structure and Receptor Binding Domain, Gary K. Schoolnik, Rosemary Fernandez, Joseph Y. Tai, Jonathan Rothbard and E. C. Gotschlich, Journal of Experimental Medicine, vol. 159, May 1984, pp. 1351–1370.
Strain-Specific and Common Epitopes of Gonococcal Pili, Jonathan B. Rothbard, Rosemary Fernandez and Gary K. Schoolnik, Journal of Experimental Medicine, vol. 160, Jul. 1984, pp. 208–221.
Antibodies to Peptides Corresponding to a Conserved Sequence of Gonococcal Pilins Block Bacterial Adhesion (Immunogenicity/syntheticpeptiedes/reverse turns/gonococcal vaccine), Jonathan B. Rothbard, Rosemary Fernandez, Lena Wang, Nelson N. H. Teng, and Gary K. Schoolnik, Proc. Natl. Acad. Sci. U.S.A., vol. 82, Feb. 1985, Microbiology, pp. 915–919.
Pili of Neisseria Menigitidis, David S. Stephens, Anne M. Whitney, Jonathan Rothbard and Gary K. Schoolnik, Journal of Experimental Medicine, vol. 161, Jun. 1985, pp. 1539–1553.
Anigenic Analysis of Gonococcal Pili Using Monoclonal Antibodies, Mark Edwards, Ralph L. McDade, Gary Schoolnik, Jonathan B. Rothbard and Emil C. Gotschlich, J. Ejxp., Copyrighted The Rockefeller University Press, vol. 160, Dec. 1984, pp. 1782–1791.
New Hope for Pinkeye Control, Reprinted with permission from Aug. 1983, Beef, Copyrighted 1983, by Webb Agricultural Publications.

*Primary Examiner*—Howard E. Schain
*Attorney, Agent, or Firm*—Luedeka, Hodges & Neely

[57] ABSTRACT

A vaccine for immunizing cattle against infectious bovine keratoconjunctivitis which contains protein fragments having an antigenic site common to pili of pathogenic strains of *Moraxella bovis* and is produced by reacting purified *Moraxella bovis* pili with cyanogen bromide.

6 Claims, No Drawings

VACCINE AGAINST INFECTIOUS BOVINE KERATOCONJUNCTIVITIS

The invention relates to vaccines for immunizing cattle against infectious bovine keratoconjunctivitis and to methods for producing such vaccines.

Infectious bovine keratoconjunctivitis (IBK), also known as "pink eye", is a severe ocular infection of cattle which produces annual losses totaling in the hundreds of millions of dollars in this country alone. IBK is found world wide and affects all breeds and ages of cattle. The disease can cause the animals to go temporarily blind and they do not feed resulting in a loss of weight gain in beef cattle and poor milk production in dairy cattle.

The etiological agent of IBK is the bacterium *Moraxella bovis* (*M. bovis*). Pathogenic strains of *M. bovis* have hair-like structures called pili projecting from the surface of the bacteria which allow the bacteria to adhere to the cells covering the bovine eye.

Known treatments of IBK generally require the direct application of antibiotics to the eyes of the animal. The treatments are not always effective and are both time consuming and expensive. Vaccines have also been developed but, due to the numerous serotypes of *M. bovis*, inoculation with known vaccines has not provided effective immunity against infection by all strains. Vaccines composed of purified pili from one *M. bovis* strain have been shown to provide immunity to infection by strains of the bacterium closely related to those used to prepare the vaccine but not to other heterologous strains.

Other attempts to produce a vaccine against all strains have employed killed cells or purified pili from more than one strain. For example, the vaccine sold under the trademark PILIGUARD by Shering Corporation, Kenilworth, N.J., is a formalin-inactivated whole cell bacterin produced from two *M. bovis* strains, EPP 63 and FLA 64. Another approach to the production of a vaccine has been to include purified pili from different *M. bovis* strains (preferably six or more) such as is disclosed in European Application Publication No. EP 0 107 845 A2.

It is accordingly an object of the present invention to provide a vaccine which is effective for immunizing cattle against all strains of *M. bovis*.

The vaccine according to the invention contains a pharmaceutically acceptable carrier and protein fragments having at least one antigenic site common to pili proteins of pathogenic strains of *Moraxella bovis*. The protein fragments are capable of inducing the production of antibodies reactive to the common antigenic site. Cattle are inoculated with the vaccine to develop immunity against infection by homologous and heterologous strains of *M. bovis*.

The protein fragments have peptide sequences corresponding to antigenic determinants of pili proteins which are normally immunorecessive and an immune response is not typically elicited to such determinants when cattle are exposed to *M. bovis*. The protein fragments are prepared from *M. bovis* pili proteins by reaction of the pili proteins with cyanogen bromide which cleaves the pili proteins and produces fragments with exposed common antigenic sites. Alternately, using recombinant DNA techniques, a DNA sequence encoding the common antigenic sites can be cloned and the DNA expressed in a suitable host to produce the protein fragments.

Since the antigenic sites of the protein fragments are believed to be common to all pathogenic strains of *M. bovis*, the fragments for preparing the vaccine can be obtained from the pili of many different *M. bovis* strains and suitable strains are, for example, NPTn, IBH-64, FLA-64 and EPP-63. *M. bovis* strains can be grown by known procedures such as on tryptose blood agar base (Gibco Diagnostics, Madison, WI) supplemented with 5% bovine blood and harvesting by scraping the agar surface. For continuous production, it is necessary to maintain the organism in piliated form by selecting and cloning the colonies which are flat, hemolytic and indent the agar below them.

For production of the vaccine from *M. bovis* pili, *M. bovis* pili are preferably isolated from other cellular components before reaction with cyanogen bromide. This is accomplished by placing the bacteria in a hypotonic buffer (0.01 M Tris pH 9.5) and shearing the pili from the cells by agitation with a homogenizer and removing the cells by centrifugation. The pili are purified by repeated alternate treatments of centrifugation in hypotonic buffer and isotonic buffer (0.05 M Tris in physiologic saline, pH 8.0) and the pili are collected in the pellet from the isotonic buffer.

The reaction with cyanogen bromide is preferably performed so that substantially all of the pili protein is cleaved with cyanogen bromide at methionine residues. The reaction is suitably performed by contacting the purified pili in 0.1 N HCl with cyanogen bromide (50 mg./5ml) overnight. The resulting solution is lyophilized to remove the remaining cyanogen bromide and hydrochloric acid and to concentrate the fragments to a suitable concentration.

Depending on the strain of *M. bovis*, three to five different fragments typically result from the cleavage of pili proteins with cyanogen bromide. Shared antigenic determinants are present on one or more of these fragments. The entire product of the cyanogen bromide reaction which has been concentrated as necessary can be employed in producing a vaccine according to the present invention. In addition, it is believed that an effective vaccine can contain selected fragments which elicit the production of antibodies to the common antigenic sites. Selected fragments can be isolated from the other fragments produced by the cyanogen bromide reaction by preparative polyacrylamide gel electrophoresis or by reverse phase high-pressure liquid chromatography.

The vaccine in accordance with the invention is preferably in a form suitable for parenteral administration such as intramuscular or subcutaneous injection or for injection into the lacrymal gland or the third eyelid. The protein fragments are contained in, for example, a pharmaceutically acceptable buffer solution in which the protein fragments are dissolved and containing, as desired, other components such as adjuvants and preservatives. A suitable adjuvant is aluminum hydroxide and preservatives such as formalin or gentamicin can be included in concentrations conventionally used in vaccines.

The vaccine according to the invention can be used similarly to the commercially available vaccines for IBK. Preferably, the vaccine is administered in a manner which promotes the production of secretary immuoglobulin A (S-IgA) such as by lacrymal gland injection. The concentration of the protein fragments in the vaccine is adjusted in accordance with the intended mode of administration with a minimum concentration for effectively stimulating antibody production. For intramuscular or subcutaneous injection, the concentration is adjusted such that an injection of 2-3 ml is sufficient. For lacrymal gland or third eyelid injection, the vaccine is prepared so that an injection of about 0.5 ml is sufficient.

The following examples are offered to illustrate the invention and are not intended to be limiting.

EXAMPLE I

Growing and Harvesting M. bovis Bacteria

M. bovis strains NPTn, IBH-64, FLA-64, and EPP-63 are grown on tryptose blood agar base supplemented with 5% bovine blood (BBA). The organism is maintained in piliated form by selection and cloning of colonies which were flat, hemolytic, and indented the agar. Any non-piliated variants of *M. bovis*, characterized by rounded colonies which do not indent the surface of the agar, are discarded. The bacteria are either kept frozen at −70C. in 40% glycerol in trypticase soy broth (Gibco Diagnostics, Madison, WI), or are subinoculated every 24 hours on BBA and incubated overnight at 37C. The bacteria for harvesting are prepared by picking up colonies from overnight cultures with sterile cotton swabs and streaking them onto BBA in stainless steel pans (20 cm wide by 37 cm long). The bacteria are harvested after overnight incubation at 37° by scraping the surface of the agar with a microscope slide.

EXAMPLE II

Pilus Isolation and Purification

Harvested cells of each strain of Example I are suspended in 60 mls of 0.05 M. Tris buffered physiological saline (pH 8.0) with 0.01 M sodium azide (TBS) on ice. The bacteria are washed once in this buffer by centrifugation at 13,000 g for 30 minutes at 4° C. Sodium azide is included in the buffer to prevent bacterial growth in the preparation. The pellet is resuspended in 60 mls of ice cold 0.01 M. Tris buffer (TB) (pH 9.5) with 0.01 M sodium azide and the pili are sheared from the cells by agitation with a homogenizer (Virtis Model 23, Virtis Company, Gardiner, NY) at 70% speed for 5 minutes at 4° C. The cells are pelleted and removed by centrifugation at 13,000 g for 30 minutes. The supernatant fluid is dialyzed overnight at 4° C. in 6,000 to 8,000 mw cut-off dialysis tubing (Spectrapor I Membrane Tubing, Spectrum Medical Industries, Inc., Los Angeles, CA) against 2 liters of 0.05 M TBS. A pilus-rich precipitate forms and is collected by centrifugation at 13,000 g for 1 hour, and is resuspended in 30 mls of 0.01 M TB. Material which does not redissolve is pelleted and removed by centrifugation at 23,000 g for 1 hour at 4° C. The supernatant fluid constitutes the pilus suspension which is dialyzed again. Alternating cycles of differential centrifugation and dialysis are repeated twice more until the pilus preparation is free of cellular contaminants.

The resulting pilus preparations are analysed by SDS-PAGE. Pilus preparations are diluted at four-fold with sample buffer (0.25 M Tris-HC1, 0.5% SDS, 2.5% glycerol, and 1 ug/ml bromophenol blue). These pilus preparations are held for 4 minutes at 100° C. and then are electrophoresed in a vertical slab of polyacrylamide. A 3cm stacking gel (4.0% acrylamide in 0.125 M Tris at pH 6.8) layered onto a 11.5 cm separating gel (12.0% acrylamide in 0.375 M Tris at pH 8.8) is used. All gels were 18cm wide but thicknesses varied from 0.75 mm to 3.0 mm. The current for electrophoresis is set at 10 mA for each 0.75 mm gel thickness. When the tracking dye reached the separating gel, the electric current is increased to 15 mA for each 0.75 mm gel thickness until the tracking dye reaches the bottom of the separating gel. Gels are either stained with Coomasie blue or silver stain and are photographed using positive/negative film. Estimates of pilus protein molecular weights are made by comparison of their migration distance to those of low molecular weight standards. Table 1 illustrates the apparent molecular weight by SDS-PAGE of pilus proteins isolated by the procedures of EXAMPLE II.

TABLE I

| Strain | Apparent Molecular Weight* |
|---|---|
| NPTn | 17,000d |
| IBH-64 | 17,300d |
| FLA-64 | 18,200d |
| EPP-63 | 19,200d |

*Relative to Molecular Weight Standards: bovine serum albumin - 62, 200d; ovalbumin - 45,000d; carbonic anhydrase - 31,000d; soybean trypsin inhibitor - 21,500d; and lysozyme - 14,000d.

EXAMPLE III

Protein Cleavage by Cyanogen Bromide

Purified pili of strains EPP-63, NPTn, FLA-64, and IBH-64 of EXAMPLE II are cleaved at methionine residues with cynaogen bromide. Approximately 3 mg of pilin in 0.01 M Tris buffer (pH 9.5) is mixed with 5 ml of 0.1 M HCl (final concentration) to which 50 mg of cyanogen bromide is added. The mixture is incubated overnight at room temperature, is diluted to 20 ml with distilled water and is lyophilized to concentrate the preparation and to remove the remaining cyanogen bromide and hydrochloric acid.

SDS-PAGE as performed as in EXAMPLE II reveals that EPP-63 cyanogen bromide cleaved pilus preparations produces protein fragments shown in the gel as three peptide bands, one being the uncleaved pilus protein and two bands PF-1 and PF-2 resulting from cleavage at methionine residues.

Cyanogen bromide cleaved NPTn and IBH-64 produces four major bands. Three of the bands are similar to the three bands of EPP-63 with the fourth band representing partially cleaved pilin. An additional band of small molecular weight is sometimes present.

Western Blotting

The cleaved pilus preparations are analyzed by Western Blotting employing rabbit antiserum to whole and cleaved pili from NPTn and IBH-64 prepared in accordance with known techniques. The gels of the cyanogen bromide cleaved EPP-63, NPTn, and IBH-64 pilus preparations are electroblotted onto nitrocellulose membranes by the following procedures.

The gels and sheets of nitrocellulose paper are soaked separately for 5 minutes in blotting buffer (25 mM Tris, 192 mM glycine, pH 8.3). The gels and nitrocellulose sheets then are sandwiched between two fiber pads and are placed in the apparatus with the nitrocellulose membrane facing the anode. Electrophoretic transfers of pilus proteins and protein fragments from gels to nitrocellulose are done overnight at 200 mA and 20C. The nitrocellulose membranes are then rinsed for 10 minutes in Tris buffered saline (TBS) (20mM Tris, 500 MM NaC1, pH 7.5) and are incubated in 3% w/v gelatin in TBS to block nonspecific immunoglobulin adherence.

The membrane is transferred to a second container containing the appropriate antiserum prepared in 200 ml of 1% w/v gelatin in TBS and is incubated for 1 to 2 hours at room temperature. Following a brief rinse with deionized water and two ten minute washes in 0.05% (v/v) Tween-20 in TBS, the membrane is incubated for 1 hour in affinity purified goat anti-rabbit IgG horseradish peroxidase (HRP) conjugate (BioRad Laboratories, Richmond, CA) diluted according to the manufacture's recommendations. The membrane is rinsed, washed as before and then incubated in HRP color development solution (60 ug 4-chloro-1-naphthol, (BioRad Laboratories, Richmond, CA) 20 ml methanol, and 100 ml of 0.6% v/v $H_2O_2$ in TBS) for 5 to 45 minutes. The membrane then is washed with deionized water for 10 minutes, dried between sheets of filter paper, and photographed as described previously.

Tables 2, 3, and 4 illustrate the results.

TABLE 2

Western Blot Analysis of NPTn Pilin and Cyanogen Bromide-cleaved Pilin Reacted with Rabbit Antisera to Cyanogen Bromide-Treated and Untreated Pilin from *M. bovis* Strains NPTn and IBH-64

| Antiserum | NPTn Pilin | | |
|---|---|---|---|
| | UTP[a] | PF-1[b] | PF-2[c] |
| NPTn-whole pilin | 4+[d] | + | + |
| NPTn CNBr-treated pilin | 4+ | 4+ | 4+ |
| IBH-64-whole pilin | 2+ | 0 | 0 |
| IBH-64 CNBr-treated pilin | 4+ | 1+ | 3+ |

[a]Untreated pilin
[b]Pilin fragment 1
[c]Pilin fragment 2
[d]Reaction intensity was rated subjectively with 1+ being a weak reaction and 4+ the maximal reaction.

TABLE 3

Western Blot Analysis of EPP-63 Pili and Cyanogen Bromide-cleaved Pilin Reacted with Rabbit Antisera to Cyanogen Bromide-Treated and Untreated Pilin from *M. bovis* Strains NPTn and IBH-64

| Antiserum | NPTn Pilin | | |
|---|---|---|---|
| | UTP[a] | PF-1[b] | PF-2[c] |
| NPTn-whole pilin | ± | 0 | 0 |
| NPTn CNBr-treated pilin | 4+ | 3+ | 4+ |
| IBH-64-whole pilin | ± | 0 | 0 |
| IBH-64 CNBr-treated pilin | 4+ | 1+ | 4+ |

[a]Untreated pilin
[b]Pilin fragment 1
[c]Pilin fragment 2
[d]Reaction intensity was rated subjectively with 1+ being a weak reaction and 4+ the maximal reaction.

TABLE 4

Western Blot Analysis of IBH-64 Pili and Cyanogen Bromide-cleaved Pilin Reacted with Rabbit Antisera to Cyanogen Bromide-Treated and Untreated Pilin from *M. bovis* Strains NPTn and IBH-64

| Antiserum | NPTn Pilin | | |
|---|---|---|---|
| | UTP[a] | PF-1[b] | PF-2[c] |
| NPTn-whole pilin | 2+ | 0 | 0 |
| NPTn CNBr-treated pilin | 4+ | 4+ | 4+ |
| IBH-64-whole pilin | 3+ | 2+ | ± |
| IBH-64 CNBr-treated pilin | 4+ | 4+ | 4+ |

[a]Untreated pilin
[b]Pilin fragment 1
[c]Pilin fragment 2
[d]Reaction intensity was rated subjectively with 1+ being a weak reaction and 4+ the maximal reaction.

INDIRECT IMMUNOFLUORESCENCE

Suspensions of the four strains of bacteria from EXAMPLE I are made in deionized water. Ten drops of the suspensions are placed on ethanol-cleaned glass microscope slides, are allowed to air dry, and are fixed for one minute in absolute methanol. Doubling antiserum dilutions are made in PBS from 1:10 to 1:2, 560 using the rabbit antiserums as shown in TABLE 5. A drop of each antiserum dilution is placed on a spot of bacteria and incubated ten minutes at 37° C. in a humid chamber. The slides are washed thrice for five minutes in PBS-Tween 20 and are air dried. Goat anti-rabbit IgG fluorescein isothiocyanate conjugate (used at the highest dilution in PBS which still resulted in maximal fluorescence) is placed on the spots, is incubated and washed. The slides are examined and photographed with a photomicroscope using epifluorescence and a 40X plan-neofluar objective. Antibody titers are expressed in TABLE 5 as the inverse of the highest serum dilution which resulted in "1+" fluorescence. Intensity of fluorescence was rated subjectively from ±(minimal fluorescence) to 4+(maximal brightness).

TABLE 5

Indirect Fluorescent Antibody Titers of Rabbit Anti-*Moraxella Bovis* Pilus Sera to Homologous and Heterologous Strains of *Moraxella Bovis*

| | Strains of *Moraxella bovis* | | | |
|---|---|---|---|---|
| Antisera | NPTn | IBH-64 | FLA-64 | EPP-63 |
| NPTn-whole pilin | >2,560 | <10[a] | <10[a] | <10[a] |
| NPTn-cleaved pilin | 1,280 | 320 | 1,280 | 1,280 |
| NPTn cleaved pilin fragment 1 | 320 | 320 | 160 | 320 |
| NPTn cleaved pilin fragment 2 | 320 | 160 | 160 | 160 |
| IBH-64 whole pilin | 160[b] | 1,280 | <10[c] | 160[b] |
| IBH-64 cleaved pilin | 1,280 | >2,560 | 640 | 640 |
| FLA-64 whole pilin | 80[c] | 80[c] | >2,560 | 80[c] |
| FLA-64 cleaved pilin | 640 | 1,280 | >2,560 | 320 |
| normal rabbit serum | <10[d] | <10[d] | <10[d] | <10[d] |

[a]Titer of 1,280 to cells.
[b]Titer of 160 to cells.
[c]Titer of 320 to cells.
[d]No fluorescence to any part of the cell was seen with normal rabbit serum.
*NPTn whole pilus antiserum had an antibody titer of 2,560 to a non-piliated variant of NPTn.

EXAMPLE IV

Vaccine Preparation

The lyophilized solutions containing cyanogenbromide cleaved NPTn, EPP-63, FLA-64, and IBH-64 pilus preparations are each dialyzed against potassium phosphate buffer containing gentamicin until the desired purity is achieved. The resulting purified solutions are mixed with an aluminum hydroxide solution to achieve the desired quantities of adjuvant and concentrations of protein fragments in the final vaccines.

The cleavage of pilin proteins with cyanogen bromide exposes immunogenic determinants which are immunorecessive on the uncleaved pilus protein but are common to all strains of *M. bovis.* Tables 2-4 indicate that the second major pilin fragment, PF-2, is more reactive to the IBH-64 cleaved pilin antiserum than is fragment PF-1 and it is believed that the PF-2 fragment alone can be used to produce an effective vaccine. The vaccine according to the present invention provides an effective vaccine against IBK caused by all *M. bovis* strains, both homologous to the strain used to produce the vaccines as well as heterologous strains.

What is claimed is:

1. A vaccine against infectious bovine keratoconjunctivitis comprising a pharmaceutically acceptable carrier and protein fragments derived from individual pili of a pathogenic strain of Moraxella bovis by cleaving such pili with cyanogen bromide, each such protein fragment including at least one antigenic site exposed in the course of said cleaving of said Moraxella bovis and which is common to the pili proteins of multiple pathogenic strains of Moraxella bovis, said protein fragments being capable of inducing the production of antibodies reactive to said antigenic site, said antibodies being nonspecific to the Moraxella bovis strain from which said protein fragments originated.

2. The vaccine of claim 1 wherein said protein fragments are produced by cleaving *Moraxella bovis* pili with cyanogen bromide.

3. The vaccine of claim 2 wherein the Moraxella bovis pili are derived from *M. bovis* strains selected from the class consisting of NPTn, EPP-63, IBH-64 and FLA-64.

4. The vaccine of claim 2 wherein said protein fragments are produced from *Moraxella bovis* pilus preparations substantially free of other cellular components.

5. A method for producing a vaccine against infectious bovine keratoconjunctivitis comprising producing a supply of *Moraxella bovis* bacteria, concentrating pili from said bacteria, cleaving said pili with cyanogen bromide to produce fragments, and mixing said fragments with a pharmaceutically acceptable carrier.

6. The method of claim 5 further comprising purifying said pili to be substantially free of other cellular components before cleaving said pili with cyanogen bromide.

* * * * *